United States Patent
Estrella De Castro et al.

(10) Patent No.: US 7,045,643 B2
(45) Date of Patent: May 16, 2006

(54) METHOD FOR OBTAINING NOVEL LUTEIN-BASED FORMULATIONS

(75) Inventors: Antonio Estrella De Castro, León (ES); Nieves Fraile Yecora, León (ES); Manuel Oliver Ruiz, León (ES); Angel Muñoz, León (ES); Juan Francisco Lopez Oritz, León (ES); Walter Cabri, León (ES)

(73) Assignee: Vitatene, S.A., Leon (ES)

( * ) Notice: Subject to any disclaimer, the term of this patent is extended or adjusted under 35 U.S.C. 154(b) by 7 days.

(21) Appl. No.: 10/498,434

(22) PCT Filed: Dec. 20, 2002

(86) PCT No.: PCT/ES02/00609

§ 371 (c)(1),
(2), (4) Date: Dec. 2, 2004

(87) PCT Pub. No.: WO03/055855

PCT Pub. Date: Jul. 10, 2003

(65) Prior Publication Data

US 2005/0079223 A1  Apr. 14, 2005

(30) Foreign Application Priority Data

Dec. 28, 2001 (ES) .................................. 0102917

(51) Int. Cl.
*C11B 3/00* (2006.01)

(52) U.S. Cl. ...................... 554/206; 554/175; 568/838; 426/310; 426/540

(58) Field of Classification Search ................ 554/175, 554/206; 568/834; 426/810, 540
See application file for complete search history.

(56) References Cited

U.S. PATENT DOCUMENTS

| 3,523,138 A | 8/1970 | Grant |
| 5,382,714 A * | 1/1995 | Khachik ..................... 568/834 |
| 5,648,564 A | 7/1997 | Ausich et al. |
| 5,968,251 A | 10/1999 | Auweter et al. |

FOREIGN PATENT DOCUMENTS

| EP | 0 937 412 | 8/1999 |

* cited by examiner

*Primary Examiner*—Deborah D. Carr
(74) *Attorney, Agent, or Firm*—Ladas and Parry LLP

(57) ABSTRACT

The present invention describes a method of preparation of formulations of microcrystalline lutein, particularly in the form of esters, which are resistant to oxidation and are soluble in hydrophilic and/or lipophilic media. For these formulations, the esters of lutein are mixed with antioxidants, vegetable oils and/or organic solvents, and this initial mixture is submitted to various stages depending on the type of final formulation required. These formulations are suitable for direct application as colourants in the pharmaceutical, food and cosmetics fields. They can also be used as diet supplements.

30 Claims, No Drawings

METHOD FOR OBTAINING NOVEL LUTEIN-BASED FORMULATIONS

FIELD OF THE INVENTION

The present invention relates to a new methodology for production of lutein formulations, basically esters of lutein with various fatty acids, starting from any natural or synthetic source, which impart a high added value to these molecules, since they make it possible to obtain stabilized preparations thereof for direct application in the foodstuffs, pharmaceutical and cosmetics fields.

owing to their yellow to red colouration, the carotenoids are used as a food supplement and colourant in margarine, butter, oils, soups), sauces, etc. (Ninet et al., Microbial Technology, 2nd Edn, Vol. 1, 529–544 (1979), Academic Press NY, Eds. Peppler H. J. and Perlman D.).

Lutein, (3R, 3'R, 6'R)-β,ε-carotene-3,3'-diol, is a carotenoid belonging to the group of the xanthophylls or carotenoids with oxygenated functions. It is a polyunsaturated asymmetric molecule that consists of a carbon skeleton similar to that of α-carotene ((6'R)-β,ε-carotene), but having a β hydroxyl at C-3 and an α hydroxyl at C-3'. Its empirical formula is $C_{40}H_{56}O_2$ with a molecular weight of 568.85 and the following molecular formula:

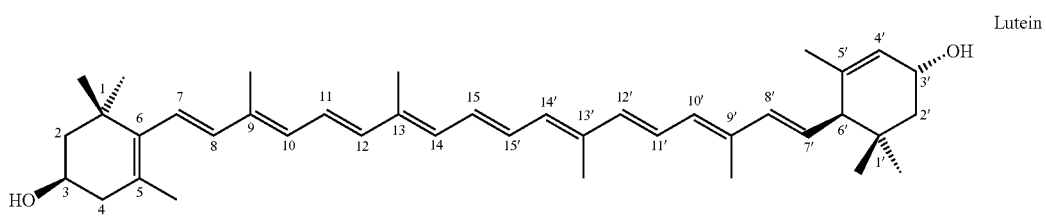

STATE OF THE ART

Traditionally, the carotenoids have been regarded as plant pigments. In fact they occur in all green tissues in the form of photosynthetic pigment-protein complexes within the chloroplasts. Despite the fact that the typical yellow to red colour of the carotenoids is masked by the green colour of the chlorophylls, the typical colouration imparted by the carotenoids can be observed in the leaves of many trees in the autumn, when the chlorophyll decomposes, and the xanthophylls are esterified by mixtures of fatty acids. With few exceptions, the carotenoids present in the majority of the leaves of all species are β,β-carotene, lutein, violaxanthin and neoxanthin. Of course, small quantities of other carotenoids may also be encountered, such as β,ε-carotene, β-cryptoxanthin, zeaxanthin, antheraxanthin, lutein 5,6-epoxide and lactucaxanthin. Many flowers or fruits (tomato, orange, peppers, marigold, etc.), displaying a colour range from yellow to red, owe their colouration to the carotenoids located in their chromoplasts, and are often present in the form esterified by fatty acids (G. Britton, S. Liaaen-Jensen, H. Pfander, Carotenoids, Volume 1A: Isolation and Analysis, 201, Publ. Birkhäuser, 1995).

The carotenoids can be divided into two classes: pure hydrocarbons, called carotenes, which include compounds such as β-carotene, α-carotene, γ-carotene or lycopene and xanthophylls, molecules that contain oxygenated functions, examples of this type being asthaxanthin, capsanthin, cantaxanthin or lutein. The two groups of compounds behave differently as regards their physicochemical properties and solubility in organic solvents.

All these compounds play an important role in the human diet, and their properties as antioxidants for the prevention of cancer and other human diseases and as precursors of vitamin A have been investigated extensively. Furthermore, In 1907, on the basis of combustion analysis, together with classical determinations of molecular weight, the molecular formula $C_{40}H_{56}O_2$ was proposed for a compound isolated from green leaves, which was called "xanthophyll" (R. Willstatter and W. Mieg, Liebig's Ann. Chem., 335, 1 (1907)). Nevertheless, the formula $C_{40}H_{56}O_2$ for the lutein isolated from egg yolk was postulated some years later (R. Willstatter and H. H. Escher, Z. Physiol. Chem., 76, 214 (1912)), and it was not known at that time that lutein and the compound isolated previously from leaves and called "xanthophyll" were the same.

Up to that moment, all attempts to elucidate the molecular structures of the carotenoids by classical experiments of chemical degradation until identifiable fragments were found, had not met with success. The highly unsaturated nature of the carotenoids was confirmed some years later (1928) by experiments of catalytic hydrogenation, and it was then that the term polyene was applied for the first time (L. Zechmeister, L. Von Cholnoky and V. Vrabély, Ver. Deut. Chem. Ges., 61, 566 (1928)). Starting from this moment, a clear and direct relation was established between colour and the number of conjugated double bonds present in these molecules (R. Kuhn and A. Winterstein, Helv. Chim. Acta, 11, 87; 116; 123; 144 (1928), and R. Kuhn and A. Winterstein, Helv. Chim. Acta, 12, 493; 899 (1929)).

The correct formula of lutein (or "xanthophyll") was established by Karrer in studies based on reactions of oxidative degradation (P. Karrer, A. Zubrys and R. Morf, Helv. Chim. Acta, 16, 977 (1933)).

The instability of the carotenoids in crystalline form is well known, and one method of stabilizing them is to prepare oily dispersions. Moreover, it is thought that when the carotenoids are dispersed in oil they are absorbed more easily by the body.

An alternative method for the stabilization of unstable compounds is their microencapsulation in starch matrices.

Thus, patents U.S. Pat. No. 2,876,160, U.S. Pat. No. 2,827,452, U.S. Pat. No. 4,276,312 and U.S. Pat. No. 5,976,575 describe a considerable increase in the stability of various compounds, including the carotenoids, by encapsulating them in a starch matrix.

One of the main difficulties in using the carotenoids in the field of colourants is their zero solubility in water, since many of their applications take place in aqueous media. This problem of solubility is mentioned in document U.S. Pat. No. 3,998,753, and was solved by preparing solutions of carotenoids in volatile organic solvents, such as halogenated hydrocarbons, and emulsifying them with an aqueous solution of sodium lauryl sulphate.

Document U.S. Pat. No. 5,364,563 describes a method of producing a preparation of carotenoids in powder form, which involves forming a suspension of a carotenoid in a high-boiling-point oil. The suspension is superheated with steam for a maximum period of 30 seconds to form a solution of carotenoid in oil. Next, this solution is emulsified with an aqueous solution of a colloid and then the emulsion is spray-dried.

In general, in the state of the art we have not found formulations of lutein that are resistant to oxidation for prolonged periods of storage and, at the same time, are soluble in lipophilic or hydrophilic media, permitting their use as colourants for foodstuffs, pharmaceuticals and in cosmetics, for example, or as diet supplements. Most of the commercial samples of lutein consist of extracts or oleoresins from plants, which have inadequate stability owing to their limited content of antioxidants. Moreover, these oleoresins are difficult to use in hydrophilic environments, owing to their zero solubility in water, so that their use is limited to applications in lipophilic environments. In contrast, our formulations exhibit high stability owing to their controlled content of antioxidants, and are perfectly applicable in both hydrophilic and lipophilic environments.

BRIEF DESCRIPTION OF THE INVENTION

The invention describes a method of formulation, finishing or final presentation of lutein, related compounds (basically esters of lutein with various fatty acids) or mixtures of both, obtained from any natural or synthetic source, depending on their final application, which consists of premixing with antioxidants in the presence of oils and/or organic solvents, in suitable proportions.

It is possible to obtain, according to this method:

A microcrystalline suspension of lutein and/or related compounds, in vegetable oil; suitable for applications in lipophilic environments.

CWD lutein (cold-water-dispersible lutein); suitable for applications in hydrophilic environments.

Each variant of the method of preparation of formulations comprises the following stages:

Microcrystalline suspension of lutein and/or related compounds in vegetable oil:
Mixing of the vegetable oil with the active molecule and an antioxidant.
Milling of the mixture. CWD lutein (cold-water-dispersible lutein):

Molecular dissolution of lutein and/or related compounds in an organic solvent, preferably in the presence of antioxidants or vegetable oils or both
Emulsifying of the organic solution of the active molecule with an aqueous solution of modified starches
Evaporation of the organic solvent and of the water until the dry residue is obtained and the appropriate level of residual solvents
Drying and finishing of the product.

The method described endows this molecule with stability that is sufficiently high (longer than 6 months in suitable conditions of packaging) to prevent its oxidation during storage.

DETAILED DESCRIPTION OF THE INVENTION

A principal object of this invention is a method of preparation of various formulations as a function of the characteristics of the application for which it is intended to use lutein and/or its related compounds. The said method consists of premixing of microcrystalline lutein with antioxidants in the presence of oils and/or organic solvents, in suitable proportions.

A first formulation, called microcrystalline suspension of lutein in vegetable oil, consists of premixing the lutein molecule to be formulated, with a variable quantity of vegetable oil. A great variety of vegetable oils can be used, and the commonest, but not the only ones, are sunflower oil, olive oil, corn oil, soya oil, cottonseed oil, etc. The dose of lutein and/or related compound will depend on the final strength it is desired to achieve, the commonest values being suspensions with a content of active principle between 5 and 60%, preferably between 10 and 30%. To increase the stability of the mixture, the usual liposoluble antioxidants are used, such as natural tocopherols, and preferably D,L-alpha-tocopherol. The proportion of this compound varies between 0.2 and 15% relative to the weight of the active molecule, preferably between 0.5 and 5%. So that the formulations containing lutein and/or related compounds have satisfactory physiological activity it is necessary to reduce the size of the crystals. This is achieved with the usual milling systems applicable to liquid mixtures. A special object of this invention is ball mills that permit reduction of crystal size below 10 microns, preferably below 5 microns and even more preferably below 2 microns, using microspheres between 0.5 and 0.75 mm in diameter. However, crystal size can vary in relation to the particular application of the suspension, in each case employing suitable spheres and milling conditions. The crystal size will also determine the rheological properties of the mixture, especially its viscosity, which can also be adjusted depending on requirements.

These microcrystalline suspensions of lutein and/or related compounds in oil are suitable for applications in lipophilic environments.

A second formulation, called cold-water-dispersible (CWD) lutein formulation, is based on the dissolution of lutein and/or related compounds in an organic solvent and their subsequent microencapsulation in modified starches. This invention will refer in particular to the use of food-grade solvents that are regarded as natural, such as acyl esters, preferably ethyl, propyl, isopropyl, butyl or isobutyl acetates, which combine the reasonably high solubility for the carotenoid components with compatibility as solvents included in the Group of Class III of the ICH. These solvents are permitted both at national and at community level, in both the pharmaceutical and the foodstuffs fields (RDL12/04/90 and RDL16/10/96). According to the ICH, the content of residual solvents must be below 5000 ppm, preferably below 1000 ppm and more preferably below 100 ppm, always based on the dry matter of the liquid mixture. The concentration of lutein and/or related compounds in the organic solvent can vary between 1 and 50 g/l, preferably between 10 and 30 g/l. The temperature of dissolution can vary between room temperature and the boiling point of the solvent, preferably between 20 and 130° C. The fact that the percentage of cis lutein is a function of the temperature/time relation in the operation of dissolution of the molecule in the organic solvent means that if we wish to obtain a product with a low content of this isomer, either a low dissolution temperature will be used, or otherwise a very short dissolution time. Thus, in order to achieve low levels of cis, and owing to the relatively low solubility of these compounds in solvents of this type (acyl esters) at temperatures of the order of 20–40° C., dissolution will preferably be effected between 70 and 130° C. for a few seconds. It should be noted that the trans isomer is the natural isomer, and that there are differences in shade of colouration between the two isomers. On the other hand, if the levels of cis isomer are not important, dissolution can be carried out without restriction on its conditions rather than achievement of complete solubility at the molecular level. Alternatively, it is possible to use a solvent with greater solubility for these molecules at relatively low temperatures (20–35° C.), such as chloroform, methylene chloride, THF, etc. In this case dissolution can be effected at low temperature (around 30° C.) for some minutes, without any risk of forming cis isomers in excessively high proportions. To increase the stability of the final formulation, an antioxidant, or mixtures of several antioxidants, preferably such as tocopherol, ascorbyl palmitate, etc., each of them in a proportion between 0.2% and 30% typically 1% to 30%, preferably between 10 and 20%, relative to the weight of the active molecule, are dissolved together with the lutein and/or related compounds in the organic solvent. It is also possible to incorporate vegetable oil in the mixture, i.e. sunflower oil, olive oil, corn oil, soya oil, cottonseed oil, etc., with the aim of promoting the dissolution of the lutein and/or related compounds, and giving the preparation additional stability. The lutein/oil ratio can vary between 10/1 and 1/10.

The solution of the active molecule thus obtained is mixed and emulsified with an aqueous solution containing an emulsifying agent, for example modified starch, more concretely esters derived from starch, preferably octenyl succinates derived from starch of various molecular weights, particularly, but not exclusively, Purity Gum 2000® from National Starch or Cleargum CO 01® from Roquette, and a microencapsulating agent, formed for example from modified starch, more concretely esters derived from starch, preferably octenyl succinates derived from starch of various molecular weights, particularly, but not exclusively, Hi Cap 100® or Capsul® from National Starch. The mixing ratio of the emulsifying agent and the microencapsulating agent can vary between 5/95 and 95/5, preferably between 25/75 and 75/25, and more preferably between 40/60 and 60/40. The water content of each of the components of the mixture of emulsifying agent and microencapsulating agent is variable, and can be between 1 and 30%, preferably between 5 and 20%, and more preferably 10%. The mixture of aqueous and organic phases is emulsified and the emulsion obtained is homogenized using pressure-difference homogenization systems of the Mantón Gaulin or Microfluidizer type, which are commonly used, and preferably by homogenization by tangential friction, for example with an emulsifier of the Ultraturrax type, for a time that varies according to the energy supplied by the equipment and the volume of mixture to be emulsified, with the aim of obtaining an average micelle size below 10 microns, preferably below 2 microns and more preferably between 0.1 and 1 micron.

Once the emulsion has formed, evaporation of the organic solvent is effected, preferably by vacuum distillation at a temperature below 50° C. As evaporation of the solvent takes place, microcrystallization of the active molecule occurs in the starch matrix. Once the solvent has evaporated, evaporation is continued, with successive additions of water until a content of residual solvents is obtained that meets the specifications for maximum concentration stipulated in the legislation, and a dry residue that is suitable for the type of drying that is to be applied to this liquid mixture. Suitable values of dry matter of the suspension of microencapsulated lutein and/or related compounds are between 1 and 30%, preferably between 10 and 25%.

It is found, in accordance with the present invention, that both the method of drying by high-temperature spraying (atomization) and the method of fluidized-bed spraying (granulation) are suitable for drying the aqueous suspension of active molecule obtained. Another alternative would be freeze-drying.

According to the method of drying by atomization, suitable inlet temperatures of the drying air would be between 100 and 200° C. whereas the outlet temperatures would be between 60 and 120° C. The atomized product has a particle size between 10 and 100 microns. In order to increase the particle size and thus reduce the available surface area, and hence increase the oxidation stability of the product, the atomized product can be submitted to a finishing process, consisting of agglomeration by spraying a solution of one of the modified starches used in the formulation, or of the actual suspension of microencapsulated active molecule within a fluidized bed of the said atomized product, making it possible to reach particle sizes in the range 50–500 microns, and preferably in the range 200–300 microns.

The granulation method involves the use of a fluidized-bed granulator in which seed material is placed, which can be a typical inert material, such as particles of sugar, or fine powder of the actual material to be dried, obtained in previous granulation operations or in a spray-drying operation. The particles are kept in motion by means of air, and the temperature of the bed is maintained between 30 and 90° C., preferably between 50 and 80° C. The suspension of lutein and/or related molecules is sprayed by means of air preheated to, a temperature between 20 and 140° C. within the fluidized bed, at a velocity that ensures that the particles to be coated are not wetted excessively and do not form lumps. The granulated product has a particle size between 100 and 2000 microns, preferably between 100 and 800 microns, and more preferably between 100 and 300 microns.

On completion of the spray-drying stage by one or other method, as well as optional agglomeration, the particles obtained can be submitted to a finishing process by coating. This coating can be effected with approximately 0.5–10% by dry weight, of aqueous solutions of sugars or even starches.

EXAMPLE 1

A laboratory ball mill of the Minizeta 003 type from Netzsch is loaded with—in this order—microspheres 0.5–0.75 mm in diameter, 30 g of sunflower oil (Koipe), 0.08 g of D,L-alpha-tocopherol (Merck) and 20 g of lutein eter Xantopina Plus (Bioquimex), which has an equivalent lutein content of 40%. The mixture was milled at 3000 rpm for 5 minutes, obtaining 45 g of an orange-coloured, viscous liquid. Spectrophotometric analysis of the oily suspension revealed a lutein content of 15%. The crystal size was less than 10 microns.

EXAMPLE 2

20 g of lutein ester Xantopina Plus (Bioquimex), which has an equivalent lutein content of 40%, was resuspended in 410 ml of isobutyl acetate, and 0.8 g of D,L-alpha-tocopherol (Merck) was added. The mixture was heated to boiling (114° C.) for 2 minutes, achieving complete dissolution of the solid. As a parallel operation, 26.65 g of Hi Cap 100® (National Starch) and 26.65 g of Purity Gum 2000® (National Starch) were dissolved in 325 ml of demineralized water. The hot organic phase was emulsified for 10 minutes in one stage over the aqueous phase using an Ultraturrax emulsifier from IKA, obtaining an average micelle size of 0.4 micron, measured with a Coulter LS230 analyser. The emulsion was transferred to a vacuum distillation system, adding 600 ml of water, so that the 410 ml of isobutyl acetate was evaporated with approximately 700 ml of water. 225 g of liquid formulation (25.9% of dry matter) was obtained with an equivalent lutein content of 2.6% (10.1% based on the dry mass). This liquid formulation was dried in an Aeromatic AG laboratory granulator, employing an inlet gas temperature of 90° C. and achieving a product temperature of 70° C., obtaining an orange-coloured powder with an equivalent lutein content of 9.7% and a water content of 2.6%.

EXAMPLE 3

20 g of lutein ester Xantopina Plus (Bioquimex), which has an equivalent lutein content of 40%, was resuspended in 410 ml of isobutyl acetate, and 0.8 g of D,L-alpha-tocopherol (Merck), 1.6 g of ascorbyl palmitate (Merck) and 8 g of sunflower oil (Koipe) were added. The mixture was heated to boiling (114° C.) for 2 minutes, achieving complete dissolution of the solid. As a parallel operation, 21.5 g of Hi Cap 100® (National Starch) and 21.5 g of Purity Gum 2000® (National Starch) were dissolved in 325 ml of demineralized water. The hot organic phase was emulsified for 10 minutes in one stage over the aqueous phase using an Ultraturrax emulsifier from IKA, obtaining an average micelle size of 0.5 micron, measured with a Coulter LS230 analyser. The emulsion was transferred to a vacuum distillation system, adding 600 ml of water, so that the 410 ml of isobutyl acetate was evaporated with approximately 700 ml of water. 205 g of liquid formulation (25.0% of dry matter) was obtained with an equivalent lutein content of 2.5% (10.0% based on the dry mass). This liquid formulation was dried in an Aeromatic AG laboratory granulator, employing an inlet gas temperature of 90° C. and achieving a product temperature of 70° C., obtaining an orange-coloured powder with an equivalent lutein content of 9.5% and a water content of 3.0%.

EXAMPLE 4

20 g of lutein ester Xantopina Plus (Bioquimex), which has an equivalent lutein content of 40%, was resuspended in 500 ml of dichloromethane, and 0.8 g of D,L-alpha-tocopherol (Merck) was added. The mixture was heated at 35° C. for 5 minutes, achieving complete dissolution of the solid. As a parallel operation, 26.65 g of Hi Cap 100® (National Starch) and 26.65 g of Purity Gum 2000® (National Starch) were dissolved in 400 ml of demineralized water. The hot organic phase was emulsified for 10 minutes in one stage over the aqueous phase using an Ultraturrax emulsifier from IKA, obtaining an average micelle size of 0.5 micron, measured with a Coulter LS230 analyser. The emulsion was transferred to a vacuum distillation system, adding 600 ml of water, so that the 500 ml of dichloromethane was evaporated with approximately 800 ml of water. 200 g of liquid formulation (26% of dry matter) was obtained with an equivalent lutein content of 2.6% (10.0% based on the dry mass). This liquid formulation was dried in an Aeromatic AG laboratory granulator, employing an inlet gas temperature of 90° C. and achieving a product temperature of 70° C., obtaining an orange-coloured powder with an equivalent lutein content of 9.8% and a water content of 2.0%.

The invention claimed is:

1. A process of obtaining a microcrystalline formulation based on lutein, or its esters of fatty acids, or mixtures thereof, derived from any source, whether natural or synthetic, consisting in
   a) dissolution of the lutein in a food-grade organic solvent in the presence of antioxidants or vegetable oils or both, at temperatures ranging 30–130° C., depending on the solvent used,
   b) emulsifying and microencapsulating the organic solution obtained in the previous step with an aqueous solution of modified starch using homogenization means,
   c) evaporating the organic solvent and the water until content of residual solvents is reduced to a level suitable for food grade commercialization and microcrystallization of lutein occurs
   d) drying and finishing.

2. A process according to claim 1, characterized in that tocopherol or ascorbyl palmitate is used as the antioxidant, in a proportion from 0.2 to 30% based on the weight of lutein in the mixture.

3. A process according to claim 1, characterized in that liposoluble antioxidant compounds are used, in a proportion between 0.5 and 10%, based on the weight of lutein in the mixture.

4. A process according to claim 1 wherein the dissolution in step (a) is carried out in the presence of a vegetable.

5. A process according to claim 1, characterized in that the organic solvent used is selected from the following: methylene chloride, chloroform, THF, ethyl acetate, propyl acetate, isopropyl acetate, n-butyl acetate or isobutyl acetate.

6. A process according to claim 1, wherein the shield of the evaporation step c) is a residual content of organic solvent below 5000 ppm, relative to the dry matter of the suspension.

7. A process according to claim 1, characterized in that starch esters, are used as the emulsifying/mocroencapsulating agents.

8. A process according to claim 1, characterized in that drying of the liquid suspension is effected by atomization at temperatures in the range 100–200° C. for the inlet air and 60–120° C. for the outlet air.

9. A process according to claim 1, characterized in that drying of the liquid suspension is effected by fluidized-bed spraying at temperatures, for the bed, in the range 30–90° C., the suspension being sprayed over the said bed with air preheated to 20–140° C.

10. A process according to claim 1, characterized in that drying of the liquid suspension is effected by freeze-drying.

11. A process according to claim 1, characterized in that finishing consists of coating the particles with aqueous solutions of various sugars, or of modified starches.

12. A formulation obtainable according to the process of claim 1, characterized in that it consists of granules of a microcrystals of lutein and/or its esters of fatty acids wherein the microcrystals have an average size, measured as average micelle size, below 10 microns, and with an average granule size in the range 100–2000 microns.

13. A formulation obtainable according to the process of claim 1, characterized in that it consists of an atomized product of microcrystals of lutein and/or its esters of fatty acids wherein the microcrystals have an average size, measured as average micelle size below 10 microns, with the average particle size of the atomized product in the range 10–100 microns.

14. A formulation obtainable according to the method of claim 1, characterized in that it consists of an agglomerate of an atomized product of microcrystals of lutein and/or its esters of fatty acids wherein the microcrystals have an average size, measured as average micelle size below 10 microns, with an average agglomerate size in the range 50–500 microns.

15. A formulation according to claim 2, characterized in that it is coated with 0.5–10% by dry weight of aqueous solutions of sugars or modified starch.

16. A process for coloring a food, pharmaceutical or cosmetic which comprises incorporating any of the formulations of claim 12 as colourants, into or on to said food, pharmaceutical or cosmetic.

17. A diet supplement comprising any of the formulations of claim 12.

18. A process according to claim 2 wherein tocopherol or ascorbyl palmitate is used as the antioxidant, in a proportion from 10–20%.

19. A process according to claim 4 in which the oil used is sunflower oil, olive oil, corn oil, cottonseed oil, peanut oil or soya oil.

20. A process according to claim 1, wherein the shield of the evaporation step c) is a residual content of organic solvent is below 1000 ppm and more preferably below 100 ppm relative to the dry matter of the suspension.

21. A process according to claim 1, wherein the shield of the evaporation step c) is a residual content of organic solvent is below 100 ppm relative to the dry matter of the suspension.

22. A process according to claim 1, characterized in that octenyl succinate derivatives of starch, are used as the emulsifying/mocroencapsulating agents.

23. A process according to claim 1, characterized in that drying of the liquid suspension is effected by fluidized-bed spraying at temperatures, for the bed, in the range 50–80° C., the suspension being sprayed over the said bed with air preheated to 20–140° C.

24. A formulation obtainable according to the process of claim 1, characterized in that it consists of granules of a microcrystals of lutein and/or its esters of fatty acids wherein the microcrystals have an average size, measured as average micelle size, below 2 microns, and with an average granule size in the range 200–800 microns.

25. A formulation obtainable according to the process of claim 1, characterized in that it consists of granules of a microcrystals of lutein and/or its esters of fatty acids, wherein the microcrystals have an average size, measured as average micelle size, between 0.1 and 1 micron, and with an average granule size in the range 100–300 microns.

26. A formulation obtainable according to the process of claim 1, characterized in that it consists of an atomized product of microcrystals of lutein and/or its esters of fatty acids wherein the microcrystals have an average size, measured as average micelle size below 2 microns, with the average particle size of the atomized product in the range 10–100 microns.

27. A formulation obtainable according to the process of claim 1, characterized in that it consists of an atomized product of microcrystals of lutein and/or its esters of fatty acids acids wherein the microcrystals have an average size, measured as average micelle size below between 0.1 and 1 micron, with the average particle size of the atomized product in the range 10–100 microns.

28. A formulation obtainable according to the method of claim 1, characterized in that it consists of an agglomerate of an atomized product of microcrystals of lutein and/or its esters of fatty acids wherein the microcrystals have an average size measured as average micelle size below 2 microns, with an average agglomerate size in the range 50–500 microns.

29. A formulation obtainable according to the method of claim 1, characterized in that it consists of an agglomerate of an atomized product of microcrystals of lutein and/or its esters of fatty acids wherein the microcrystals have an average size, measured as average micelle size between 0.1 and 1 micron, with an average agglomerate size in the range 50–500 microns.

30. A formulation obtainable according to the method of claim 1, characterized in that it consists of an agglomerate of an atomized product of microcrystals of lutein and/or its esters of fatty acids wherein the microcrystals have an average size, measured as average micelle size below 10 microns, with an average agglomerate size in the range 200–300 microns.

* * * * *